US00RE38680E

(19) United States
(12) Reissued Patent
Thong et al.

(10) Patent Number: US RE38,680 E
(45) Date of Reissued Patent: Jan. 4, 2005

(54) ARRANGEMENT FOR DETERMINING A HEART RATE BY AUTOMATICALLY ESTABLISHING THE OPTIMAL REFRACTORY TIME FOR HEART RATE DETERMINATION

(75) Inventors: Tran Thong, Lake Oswego, OR (US); Paul Wyborny, Lake Oswego, OR (US); Dennis Digby, Lake Oswego, OR (US); Nawzer Mehta, Lake Oswego, OR (US); Max Schaldach, deceased, late of Erlangen (DE)

(73) Assignee: BIOTRONIK Mess-und Therapiegeraete GmbH & Co. Ingenieurbuero Berlin, Berlin (DE)

(21) Appl. No.: 10/134,397

(22) Filed: Apr. 30, 2002

Related U.S. Patent Documents

Reissue of:
(64) Patent No.: 6,064,907
Issued: May 16, 2000
Appl. No.: 08/810,017
Filed: Mar. 3, 1997

(30) Foreign Application Priority Data

Mar. 4, 1996 (DE) ..... 196 09 365

(51) Int. Cl.[7] ..... A61B 5/024
(52) U.S. Cl. ..... 600/519; 607/14; 607/5; 607/9
(58) Field of Search ..... 600/519, 518, 600/521, 515–517, 509; 607/4, 5, 14, 9; 128/901

(56) References Cited

U.S. PATENT DOCUMENTS 4,393,877 A 7/1983 Imran et al.
4,577,633 A 3/1986 Berkovits et al.
4,895,151 A 1/1990 Grevis et al.
4,967,746 A 11/1990 Vandegriff
5,129,393 A 7/1992 Brumwell

FOREIGN PATENT DOCUMENTS

DE 2853642 6/1980

OTHER PUBLICATIONS

Medical & Biological Engineering & Computing, Jan. 1978, 16, pp. 121–123.

*Primary Examiner*—Kennedy Schaetzle
(74) *Attorney, Agent, or Firm*—Venable LLP; Catherine M. Voorhees

(57) ABSTRACT

An arrangement for determining the heart rate ($f_{RR}$) or the refractory time of the cardiac tissue, particularly for detecting tachycardia or fibrillation, has an electrode (E) for sensing heart action signals (SIG), an input stage, connected to the electrode, for processing the heart action signals, a refractory member for ascertaining a refractory time value of the arrangement, in each case after a predetermined segment of a heart action signal, and a processing device, connected to the output of the input stage or of the refractory member, for determining the rate of the heart action signals, processed with blanking of the component that occurs during the refractory time, or for determining the refractory time value of the cardiac tissue. The arrangement further includes a device which is connected at least indirectly to the output of the processing device or of the input stage for automatically adjusting the refractory time of the refractory member as a function of a previously determined value of the heart rate or of a signal parameter of a previously determined heart action signal.

6 Claims, 5 Drawing Sheets

ARRANGEMENT FOR DETERMINING A HEART RATE BY AUTOMATICALLY ESTABLISHING THE OPTIMAL REFRACTORY TIME FOR HEART RATE DETERMINATION

Matter enclosed in heavy brackets [ ] appears in the original patent but forms no part of this reissue specification; matter printed in italics indicates the additions made by reissue.

BACKGROUND OF THE INVENTION

The invention relates to an arrangement for determining the heart rate or refractory time of the cardiac tissue having an electrode for sensing heart action signals, an input stage connected to the electrode for processing the heart action signals, a refractory member for ascertaining a refractory time of the arrangement after a predetermined segment of a heart action segment, and a processing device connected to an output of the input stage for determining the rate of the heart action signals, processed by blanking components of a heart action signal that occur during the refractory time.

The frequency of the natural actions of the heart (heart rate) is of overwhelming significance in controlling heart rhythm correction devices—especially, implantable pacemakers in the treatment of bradyarrhythmias or tachyarrhythmias, but also of defibrillators and cardioversion devices. Correctly detecting this variable, especially the rate detected in the heart chamber (ventricular rate) has therefore been the subject of special development work, at least since the development of the demand-type pacemaker.

In context of this work, the known arrangements has risen for automatic gain control or adaptive threshold value processing of the heart signals used to determine the heart rate. According to known arrangements, the heart signals detect fluctuations in the heart signal amplitude (as the primary source of error in rate determination) and these fluctuations are to be compensated for.

Moreover, because of the special signal shape of the heart action signals, the use of refractory time members has become established in arrangements for determining the heart rate.

A typical heart action signal of a ventricular action, which is also known as the QRST complex, is shown in FIG. 1a: The problem that makes it expedient to use a refractory member is clearly shown in FIG. 1b in terms of two successive heart action signals: If the signals are subjected to threshold value processing, with a threshold value (symbolized by a dashed line designated "+Vt" or "−Vt" on either side of the zero signal line), or in other words if the signal components located above +Vt (or optionally below −Vt) are evaluated as a "heartbeat", mismeasurements can occur in practice, especially if the maximum amplitude in the T portion of the QRST complex is above +Vt.

To prevent such a "T-wave" next to the so-called "R-wave" from being evaluated as a separate heartbeat—an effect generally called "oversensing"—the input stage is assigned a refractory member, in which the portions of the heart action signal that in FIG. 1b are located between the vertical dot-dashed lines—which indicate the boundaries of the refractory time, or the refractory interval "REF"—are blanked out. As can be seen from the example shown in the drawing, the $T_{RR}$ spacing of the R-waves is correctly evaluated as a heartbeat interval, thus fundamentally enabling the avoidance of oversensing.

From T. Parviainen et al, "Ratemeter based on analogue divider", Med. & Biol. Eng. & Comput. 1978, 16, 121, a device for determining the heart rate is known in which optimally blanking out ("blocking") of a time segment of 20 to 70% of the heartbeat interval is contemplated, to eliminate P-waves as an interference signal.

It is also known to program the refractory time patient-specifically and thus largely to take appropriate account of the individual heart signal shape.

Especially in certain tachyarrhythmias and in transition regions between tachycardic rhythm malfunctions that have a pronounced periodic ("sinusoidal") heart signal course and heart fluttering (fibrillation), strong amplitude fluctuations between the heart signal complexes can occur in the relative amplitudes of the individual signal segments, and such heart rate fluctuations can all occur parallel to one another. Under such conditions, even with a patient-specifically programmed refractory time, oversensing or—the converse, the nondetection of R-waves ("undersensing") can no longer be reliably precluded.

SUMMARY OF THE INVENTION

The object of the invention is therefore to further develop an arrangement of the generic type referred to at the outset such that even in the case of difficult tachycardic heart rhythm malfunctions, a correct determination of the heart rate becomes possible.

This object is attained by an arrangement, as described above, further having means connected at least indirectly to the output of the processing device or of the input stage for automatically adjusting the refractory time of the refractory member as a function of a previously determined value of the heart rate or of a signal parameter of a previously determined heart action signal.

The invention encompasses the concept of automatically establishing the currently optimal refractory time for the heart rate determination from a previously determined value of the heart rate during ongoing operation of the arrangement, or by evaluating a signal shape parameter of a previously detected heart action signal.

BRIEF DESCRIPTION OF THE DRAWINGS

Advantageous further features of the invention will be described in further detail below along with the description of the preferred embodiment of the invention, in conjunction with the drawings, in which.

DETAILED DESCRIPTION OF THE INVENTION

Figure 1A:
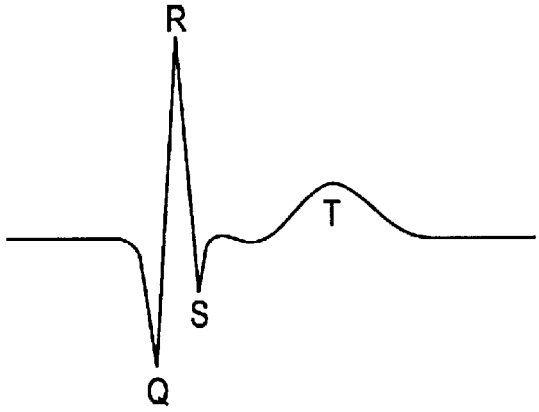
FIG. 1a is a typical heart action signal (QRST complex) in a simplified illustration.
Figure 1B:
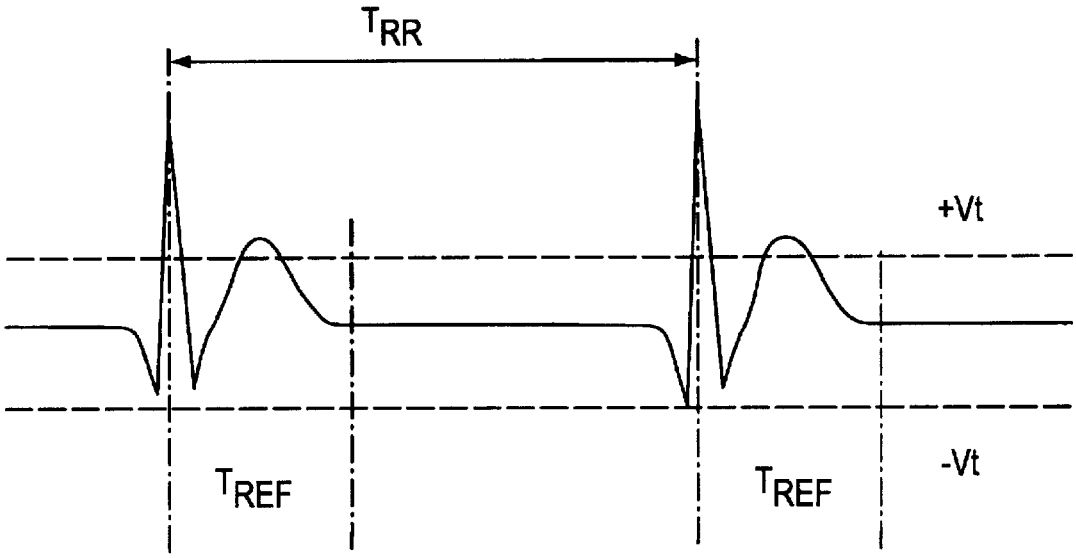
FIG. 1b is a graph to explain the effect of oversensing.

FIGS. 1a and 1b have already been explained above.

Figure 2:
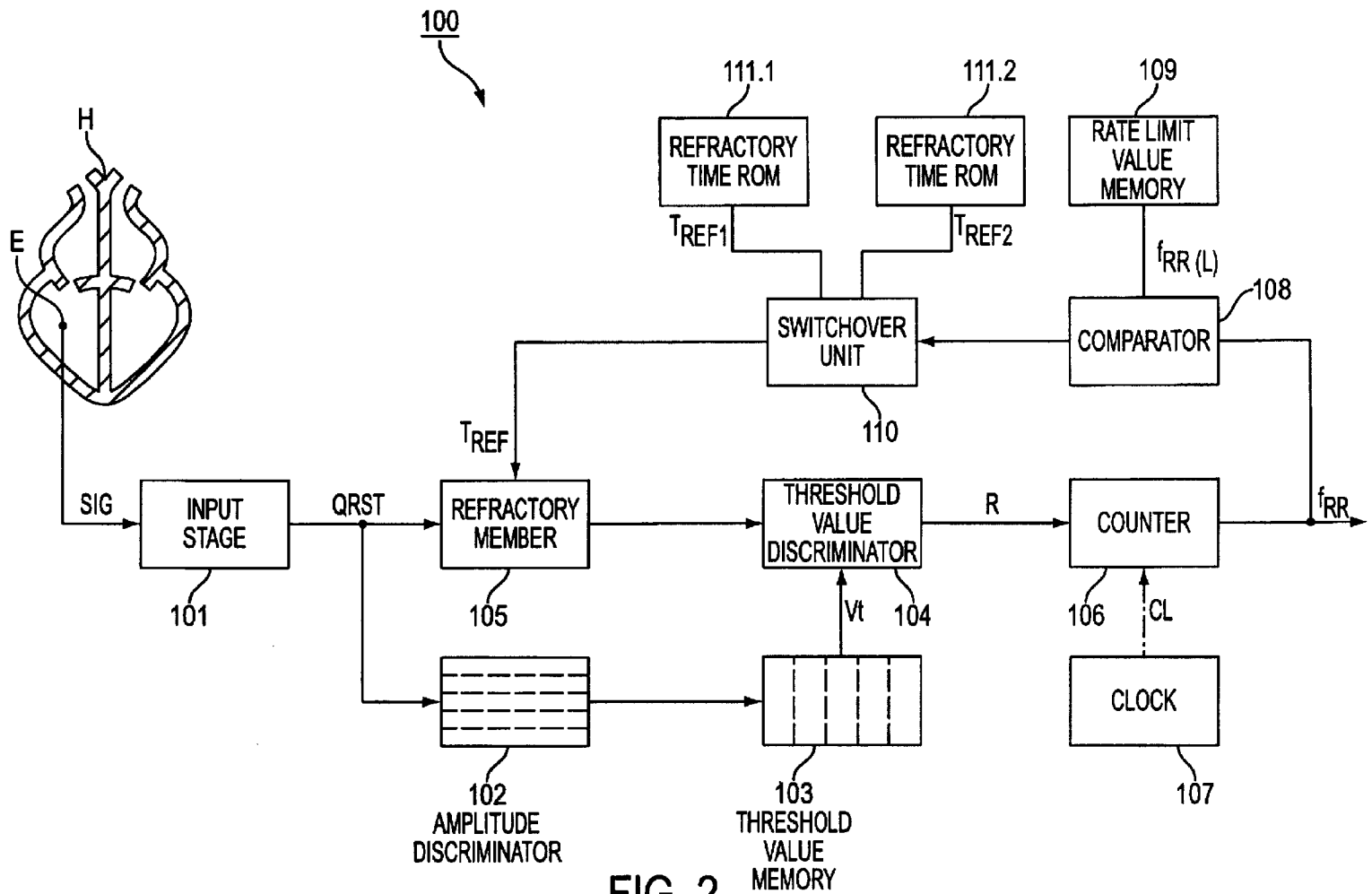
FIG. 2 is a highly simplified block circuit diagram of an arrangement according to an embodiment of the invention.

FIG. 2 is in a highly simplified block circuit diagram, shows an arrangement 100 for heart rate determination in one embodiment of the invention, which is connected to a heart H via an intracardial electrode E (that is, an electrode disposed in the ventricle). The electrode E is connected to the input of an input stage 101—known per se—with programmable filtering and amplification characteristics. Its output is connected on the one hand with the input of an amplitude discriminator stage 102, whose output is connected to the address input of a direct access threshold value memory 103. In each of its memory spaces, a heart signal amplitude value is stored as a predetermined threshold value for the heart rate determination. The data output of the threshold value memory 103 is connected to the control inputs of a threshold value discriminator 104. Its data input is connected via a refractory member or blanking circuit 105 to the output of the input stage 101, while its output is connected to the signal input of a counter 106, which is clocked by a clock generator 107.

The output of the counter 106 is connected to one input of a rate comparator unit 108, whose other input is connected to a rate limit value memory 109. The output of the rate comparator unit 108 is connected to the control input of a switchover unit 110, which is connected via two signal inputs to the data outputs of two refractory time ROMs 111.1 and 111.2 and whose output is connected to a control input of the refractory member 105.

The heart potential signal SIG picked up in the ventricle via the electrode E is subjected to filtering in order to free it of interference and to amplification in the input stage 101. As after "result"—of the filtering and amplication a result, a heart action signal QRST is available at the output of the stage 101 and is made the basis for determining the (ventricular) heart rate. The signal QRST is subjected in the amplitude discriminator 102 to classification as to the amplitude of the R-wave, and a digital signal is output that causes the addressing of a memory space in the threshold value memory 103 and the output of a previously memorized threshold value Vt to the threshold value discriminator 104.

The prepared signal QRST is also subjected in the refractory member 105 to a partial chronological blanking for the duration of a refractory time or a refractory interval $T_{REF}$, beginning with the leading edge of the R-wave. From the output signal of the stage 105, obtained as a result of the blanking, an amplitude-standardized pulse signal R is obtained in the ensuing discriminator stage 104, by means of a threshold value processing—again known per se. The successive pulse signals per unit of time are counted in the counter 106 with clocking by the clock signal CL of the clock generator 107, and as a result the output signal of the counter 106 is the ventricular heart rate $f_{RR}$.

The heart rate signal $f_{RR}$ is subjected—in addition to its use otherwise as a control signal for a heart rhythm correction device, as a diagnostic variable, or the like—to a comparison in the rate comparator unit 108 with the rate value $f_{RR}$ (L) (preferably patient-specifically programmed) stored in memory in the rate limit value memory 109. As a result of the comparison, a switching signal is output to the switchover unit 110, which in response to the switching signal connects one of the ROMs 111.1 or 111.2 with the refractory member 105, that is, delivers this one of the previously memorized refractory time values $T_{REF1}$ or $T_{REF2}$ as a valid value $T_{REF}$ for the signal blanking. The determination of suitable $T_{REF}$ values is described hereinafter.

With the above-described arrangement, a two-stage adaptation of the refractory or blanking time that is taken into account for determining the heart rate is automatically performed as a function of the current heart rate, thus reducing the danger of oversensing or undersensing.

Figure 3:
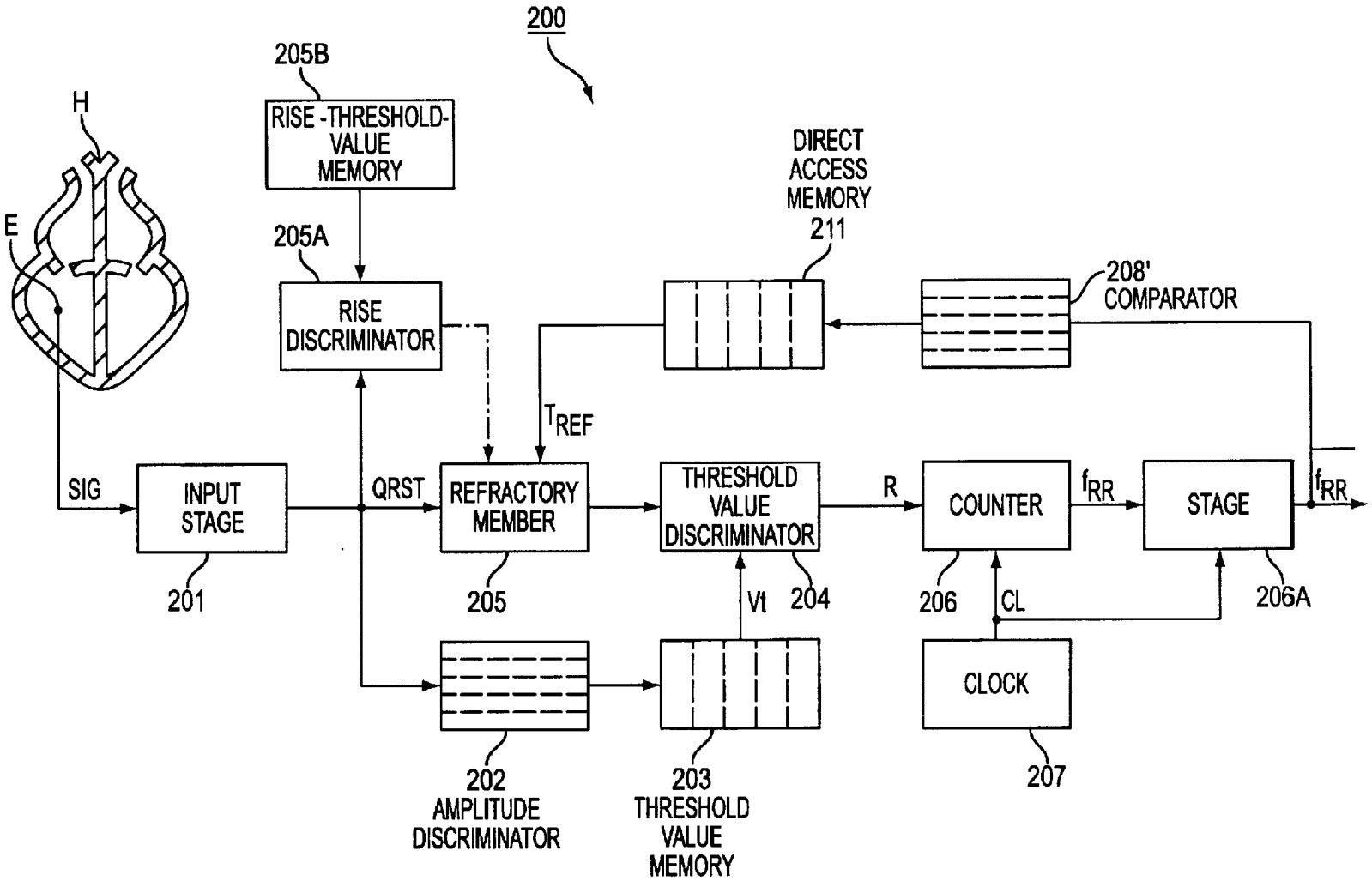
FIG. 3 is a highly simplified block circuit diagram of an arrangement in accordance with a further embodiment.

FIG. 3 is a highly simplified block circuit diagram of an arrangement 200 for determining the heart rate, which is modified compared with FIG. 2. Functionally identical or similar component groups to those of FIG. 2 are identified by corresponding reference numerals (such as 201 corresponding to 101) and will not be explained again below. The arrangement differs from that described above in that instead of two memories each for one refractory time value and one switchover device, a direct access memory 211 ("look-up table") for a plurality of refractory time values is provided, which is addressed with the output signal, derived from the current rate counting value, of a multistage rate discriminator unit 208'. In this way, by the selection from among a relatively large supply of predetermined values, finer adaptation of the refractory time to the heart rate—averaged over time in stage 206A—is made possible.

Also, the input stage 201 is followed here—parallel to the refractory member 205 and the amplitude discriminator 202—by a rise discriminator 205A, which is connected via a second input to a rise-threshold-value memory 205B and which upon detection of the leading edge of an R-wave outputs a signal, based on the rise that exceeds the memorized comparison threshold value, to activate the refractory member 205.

Figure 4:
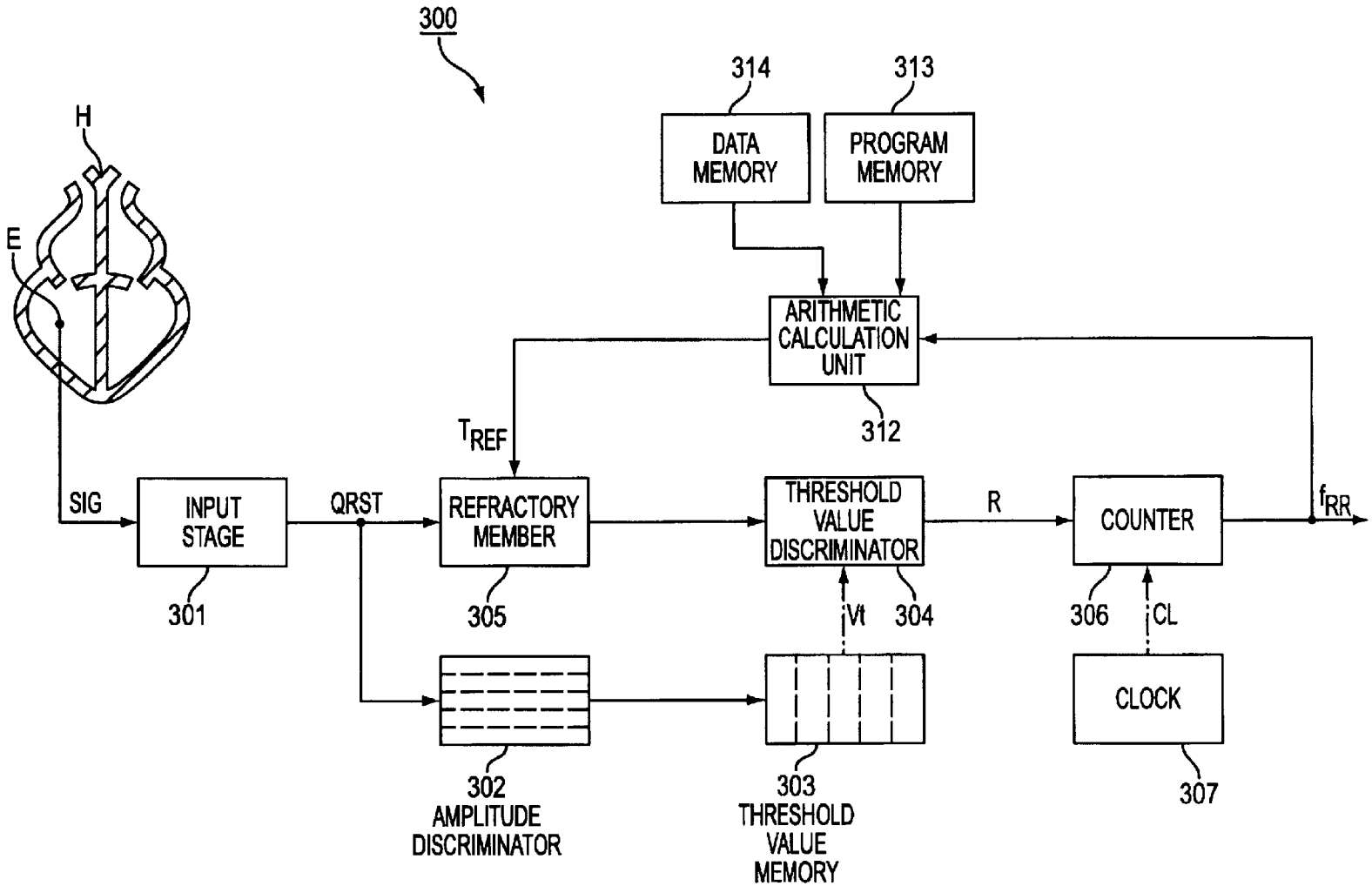
FIG. 4 is a highly simplified block circuit diagram of an arrangement in accordance with a further embodiment.

Another arrangement 300 modified over FIG. 2 is shown in FIG. 4. The arrangement 300 differs from the rate determining arrangement 100 and 200 described above in that instead of memories for preprogrammed refractory time values and access means allocated to them, an arithmetic calculation unit 312 supplied directly to the output signal of the counter 306 is provided, in which from the current rate value, the optimal refractory or blanking time value is calculated in each case on-line, in accordance with an algorithm stored in a program memory 313, and using parameter values stored in a data memory 314.

The calculation is done for instance by recourse to the equation $$QTc=QT+1.75(T_{RR}-60), \quad (1)$$

which is given in its original form by H. C. Bazett: "An analysis of the time relations of electrocardiograms", Hearts 7,353 (1920) and was later modified by other authors; in this equation a normal value for QTc is 0.41 s at $f_{RR}=60\ min^{-1}$, and is somewhat gender- and age-dependent.

Based on (1), $T_{REF}$ can be adjusted to $$T_{REF}=QT=QTc-1.75(T_{RR}-60), \quad (2)$$

in which QTc can be determined patient-specifically from electrophysiological examinations, the results of which are stored in memory. It may also be expedient to select $T_{REF}$ as a somewhat greater value than the value resulting from equation (2).

Figure 5:
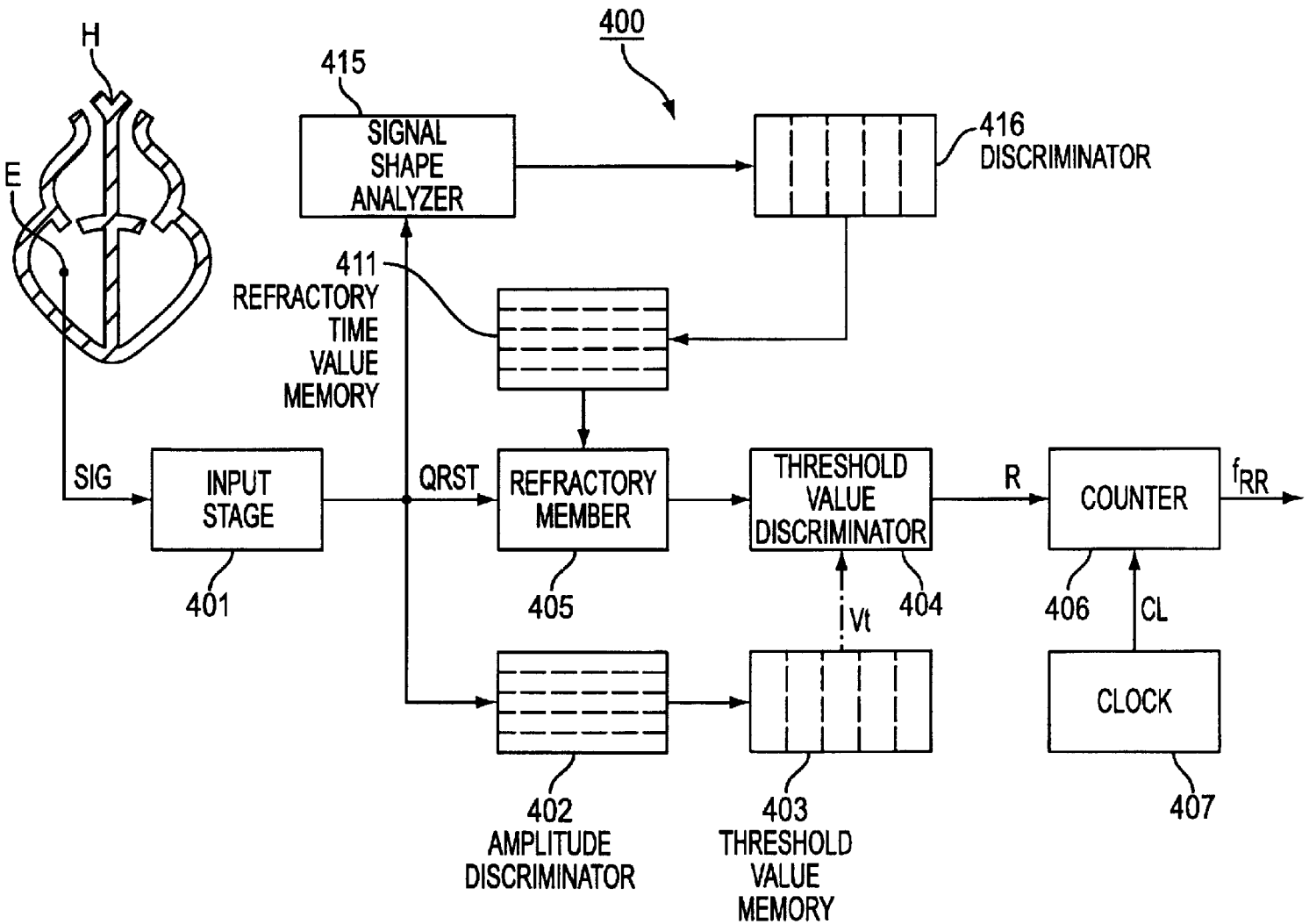
FIG. 5 is a highly simplified block circuit diagram of an arrangement in accordance with a further embodiment.

FIG. 5 shows a block circuit diagram—again highly simplified—of an arrangement 400 according to a further embodiment, in which the optimized refractory time is determined not on the basis of the most recently ascertained heart rate value but rather from a signal shape parameter of the QRST complex (such as the QR spacing, the rise of the R-wave, or the like). Once again, the function blocks largely agree with FIG. 1 (and to that extent are again given similar reference numerals).

Connected to the output of the input stage 401 is a signal shape analyzer 415, which extracts the relevant measurement variable to be derived from the signal shape. Its output is connected to a discriminator stage 416, in which the measurement variable—similarly to FIG. 3, this is the heart rate—is subject to a range classification. The output signal of the discriminator 416, which expresses the result of the classification, addresses the refractory time value memory 411, also provided here, from which the valid value is finally read out to the refractory member 405.

The above-described (or similar) arrangements may be realized in the form of independent devices or as a component of heart rhythm correction devices, in particular need-type or antitachycardia pacemakers, implantable defibrillators (AICD) or automatically controlled dosing devices for antiarrhythmia medications.

In how it is embodied, the invention is not limited to the preferred exemplary embodiments described above. On the contrary, a number of variants are conceivable that make use of the solution described even in fundamentally different types of embodiments.

What is claimed is:

1. A system for determining the heart rate and for detecting a medical condition of a heart, comprising:

an electrode for sensing heart action signals;

an input stage connected to the electrode for processing the heart action signals;

a refractory member for ascertaining a refractory time of the system after a predetermined segment of a heart action signal, said refractory member connected to an output of the input stage;

a processing device connected to an output of the input stage for determining the rate of the heart action signals which includes a means responsive to the refractory member for processing the heart action signals by blanking a component of a heart action signal that occurs during the refractory time, and a counter of detected heart signals for determining the heart rate; and adjusting means connected between an output of the processing device and said refractory member for automatically adjusting the refractory time of the refractory member which includes an arithmetic calculation unit for calculating the refractory time ($T_{ref}$) as a function of a previously determined value of the heart rate in accordance with the following equation (1):

$$[T_{ref}=QT=QTc-1.75(T_n-60)]$$

$$T_{ref}=QT=QTc-1.75(T_{RR}-60) \quad (1)$$

wherein $T_{ref}$ is the refractory period, [$T_{rr}$ is the previously calculated refractory period] *$T_{RR}$ is the time period between adjacent R-peaks of a heart action signal*, and QTc is a set period.

2. The system of claim 1, wherein a value slightly greater than the value determined by equation (1) of the arithmetic calculation unit is used to adjust the refractory time.

3. The system of claim 1, wherein the value for QTc is determined for each patient based on an electrophysiological examination.

4. An implantable cardiac pacemaker, for treating tachyarrhythmias, comprising a system according to claim 1.

5. An implantable defibrillator comprising a system according to claim 1.

6. The system of claim 1, wherein the adjusting means includes a refractory time memory addressable at least indirectly through the processing device and connected on an output side to a control input of the refractory member, the memory having a plurality of memory spaces for predetermined refractory time values.

* * * * *